US00PP28543P3

(12) United States Plant Patent
Yoshiie

(10) Patent No.: US PP28,543 P3
(45) Date of Patent: Oct. 24, 2017

(54) APPLE TREE NAMED 'MOON ROUGE'

(50) Latin Name: *Malus domestica*
Varietal Denomination: Moon Rouge

(71) Applicant: Kazuo Yoshiie, Nagano (JP)

(72) Inventor: Kazuo Yoshiie, Nagano (JP)

( * ) Notice: Subject to any disclaimer, the term of this patent is extended or adjusted under 35 U.S.C. 154(b) by 0 days.

(21) Appl. No.: 14/998,619

(22) Filed: Jan. 21, 2016

(65) Prior Publication Data

US 2016/0219767 P1 Jul. 28, 2016

Related U.S. Application Data

(60) Provisional application No. 62/107,208, filed on Jan. 23, 2015.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Lathrop & Gage LLP

(57) ABSTRACT

A new and distinct apple variety is described, the variety results from controlled cross pollination between (Jonathan× Pink Pearl)×Fuji. The fruit of the apple tree of this new variety has an attractive appearance characterized by unique color (flesh color radiates through the skin color). The new variety has been named 'Moon Rouge'.

2 Drawing Sheets

Genus and species plant claimed: *Malus domestica.*
Variety denomination: 'Moon Rouge'.

BACKGROUND OF THE INVENTION

The present invention relates to a new and distinct variety of *Malus domestica* hereinafter referred to by the cultivar name 'Moon Rouge'. The new plant variety described herein resulted from controlled cross pollination between (Jonathan×Pink Pearl)×Fuji performed in 2005 in Nagano prefecture, Japan. The controlled cross was performed in the inventor's apple orchard. Approximately 300 hybrid seeds were sown in the spring of 2006, and top grafting on 16 year-old Fuji trees ('CG24' rootstock) was performed using their scions in spring of 2007 in Nagano. The year of first bearing was 2010 and the variety was selected in 2011. The new variety was determined to be distinct from the parent varieties.

SUMMARY OF THE INVENTION

This variety can be characterized by its large size (over 300 gms grown in Japan) light pink flesh, tendency for water core and unique color (flesh color radiates through the skin color). Moon rouge displays bright white lenticels and often has water core. 'Moon Rouge' was asexually reproduced and is currently grown in Japan under Japanese conditions.

Moon rouge was determined to be distinct from the parent varieties 'Irodori' (Jonathan×Pink Pearl) and 'Fuji', as well as the closely related variety, 'Enbu' by the following characteristics. 'Moon Rouge' has yellow colored fruit skin compared with 'Irodori' which has red colored fruit skin. 'Moon Rouge' has red colored fruit fresh compared with 'Fuji' which does not. 'Moon Rouge' has yellow colored fruit skin compared with 'Enbu' which has red colored fruit skin. 'Moon Rouge' has a later harvest (late October to early/late November) than 'Pink Pearl' (mid-September).

BRIEF DESCRIPTION OF THE DRAWINGS

The accompanying colour photographs show typical specimens of the tree, foliage and fruit of the new variety as depicted in colours as nearly true as is reasonably possible to make the same in a colour illustration of this character.

DETAILED DESCRIPTION

Figure 1:
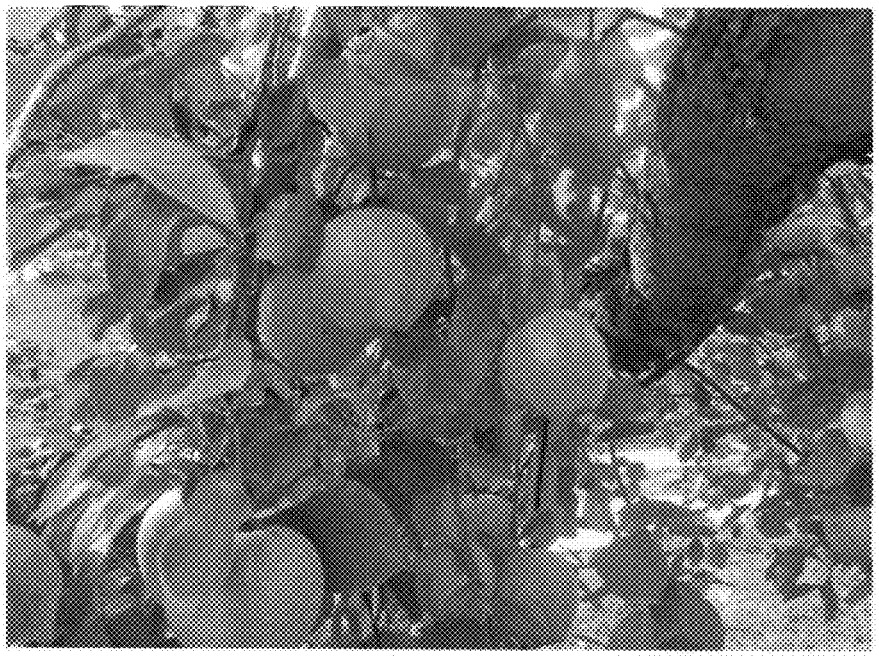
FIG. 1 shows fruit on the tree
Figure 2:
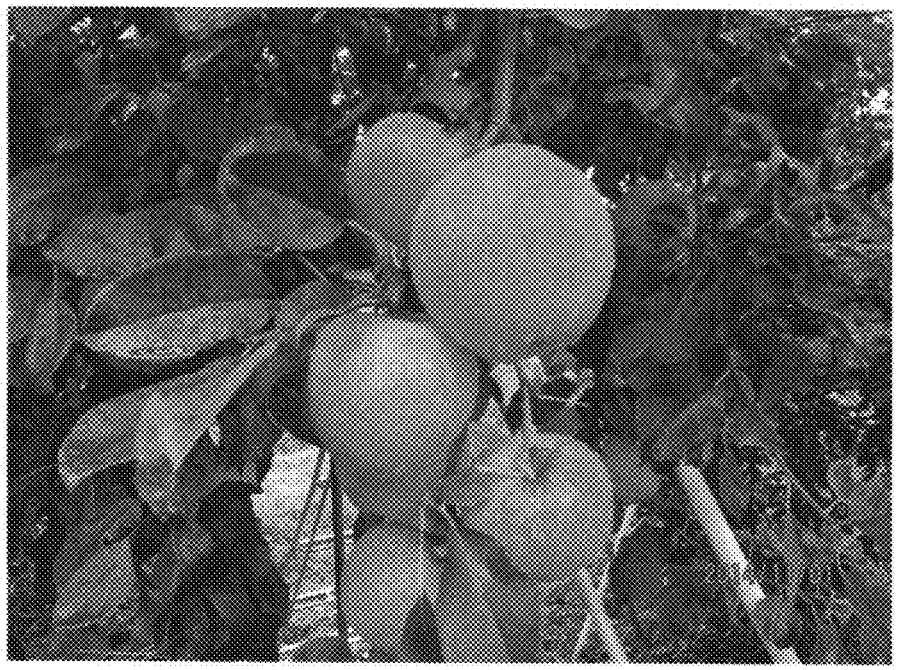
FIG. 2 shows a close up view of fruit on the tree
Figure 3:
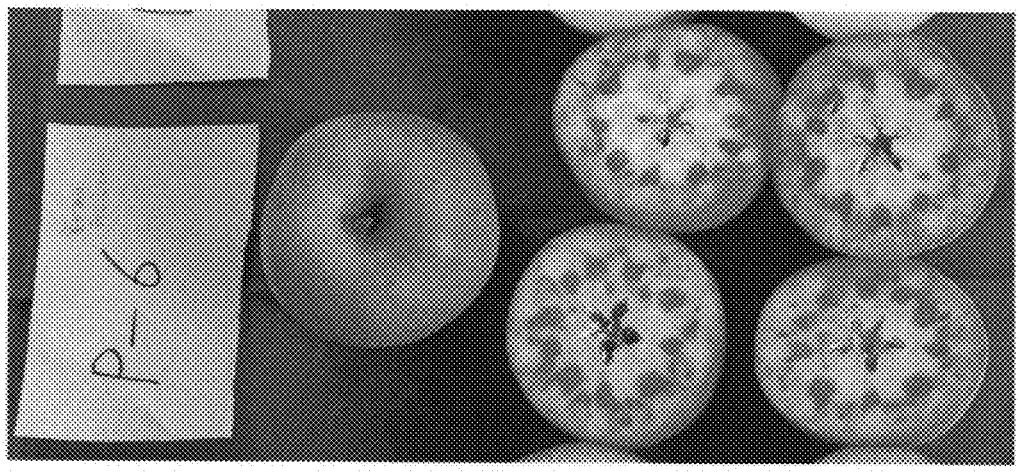
FIG. 3 shows uncut and fruit and transverse sections through fruit
Figure 4:
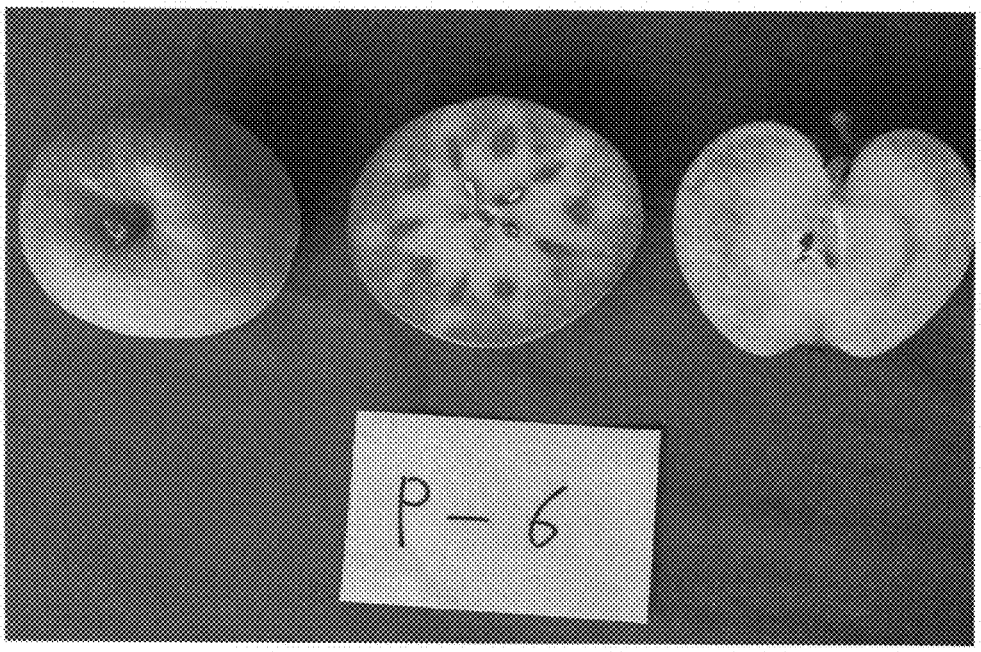
FIG. 4 shows uncut and fruit, and transverse and longitudinal sections through fruit

The following botanical description is based on observations made during the 2013 growing season in Nagano prefecture, Japan. The observations are based on top grafted (8 year-old) branches on 16 year-old 'Fuji'/CG24. Color observations are made in accordance with the Japan Horticultural Standard Color Chart (JHSCC). The following is a detailed description of the new variety:

Plant description:

*Breeding.*—Produced by controlled pollination. Parents: (Jonathan×Pink Pearl)×Fuji. Pollination self-incompatibility group: S3S9. Method of propagating the variety: vegetative propagation through grafting.

*Tree type.*—Ramified. Tree habit: spreading. Trunk (bark): grayish brown, 1317 (JHSCC). Branches: grayish brown, 1317 (JHSCC). Height (5 year old tree): 3.9 m. Trunk diameter (at 30 cm above the graft) 8.6 cm.

Foliage description:

*Length of internode (one-year-old shoot).*—Short(2.7 cm). Number of lenticels (one-year-old shoot) few. Lenticel shape: round. Lenticel number/cm$^2$: 12.4. lenticel color: pale reddish yellow, 2202 (JHSCC). Color (one year-old shoot): dark grayish brown, 1318 (JHSCC).

*Leaf blade attitude in relation to shoot.*—Upwards. Leaf blade length: medium (8.8 cm). Leaf color: deep yellow green, 4006 (JHSCC).

*Leaf blade width*.—Medium (5.7 cm). Leaf blade ratio length/width: medium (1.54).

*Petiole length*.—Short (2.7 cm).

Flower description:

*Predominant color at balloon stage*.—Strong pink, 0105 (JHSCC). Diameter with petals pressed into horizontal position: small (3.5 cm). Arrangement of petals: free.

*Time of beginning of flowering* (10% *open flowers*).—Medium.

Fruit:

*Fruit size*.—Very large. Weight (360 g under Japanese cultivating technique). Height: tall (8.5 cm). Diameter: large (9.5 cm). Ratio height/diameter: medium (0.89). Size of eye: small. Bloom of skin: moderate. Intensity of over colour: light with mixed orange-green colouring. Area of russet around stalk attachment: absent or small. Area of russet around eye basin: absent or small. Fruit skin color: bright yellow orange, 1906 (JHSCC).

*Length of stalk*.—Long (2.5 cm) Thickness of stalk: medium (2.0 mm). Depth of stalk cavity: deep (2.3 cm). Width of stalk cavity: medium (4.5 cm). Depth of eye basin: medium (0.6 cm). Width of eye basin: medium (2.8 cm). Aperture of locules (in transverse section): fully open.

*General shape of fruit*.—Ovoid. Relative area of over colour of fruit: medium (Gala). Observed dates for harvest period: late October to early/late November, Nagano prefecture, Japan. Hue of under colour (bloom removed): orange/pink/bright white lenticels. Pattern of over colour: flushed and mottled. Time of eating maturity: late (Fuji). Color of flesh is strong purplish red, 9705 (JHSCC). Acidity of flesh is low. Titlate acidity: 0.52%. Soluble solids: 14.2%. Firmness: 15.8 lb.

*Duration of storage*.—Common and cold storage is very long. Cold storage: two months. Shelf life: two weeks.

*Disease susceptibility*.—No known resistances to pests and diseases.

I claim:

1. A new and distinct apple tree substantially as illustrated and described herein.

* * * * *